US008293280B2

(12) United States Patent
Ansari et al.

(10) Patent No.: US 8,293,280 B2
(45) Date of Patent: Oct. 23, 2012

(54) METHOD FOR TREATMENT OF HIV INFECTION

(75) Inventors: Aftab A. Ansari, Atlanta, GA (US); M. Eric Gershwin, Davis, CA (US)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 914 days.

(21) Appl. No.: 11/792,334

(22) PCT Filed: Dec. 15, 2005

(86) PCT No.: PCT/US2005/045338
§ 371 (c)(1),
(2), (4) Date: Sep. 7, 2007

(87) PCT Pub. No.: WO2006/065947
PCT Pub. Date: Jun. 22, 2006

(65) Prior Publication Data
US 2008/0112978 A1    May 15, 2008

Related U.S. Application Data

(63) Continuation-in-part of application No. 11/015,631, filed on Dec. 17, 2004, now abandoned.

(51) Int. Cl.
*A61K 35/12* (2006.01)
*A61K 35/36* (2006.01)
(52) U.S. Cl. .............................. 424/520; 424/574
(58) Field of Classification Search .............. None
See application file for complete search history.

(56) References Cited

U.S. PATENT DOCUMENTS

| 4,985,254 A | 1/1991 | Konishi |
| 4,985,354 A | 1/1991 | Toyomaki et al. |
| 4,996,988 A | 3/1991 | Ohhara et al. |
| 5,013,558 A | 5/1991 | Konishi |
| 5,057,324 A | 10/1991 | Shibayama et al. |
| 5,534,509 A | 7/1996 | Konishi et al. |
| 5,560,935 A | 10/1996 | Konishi et al. |
| 5,658,896 A | 8/1997 | Konishi et al. |
| 5,807,951 A | 9/1998 | Konishi et al. |
| 6,051,613 A | 4/2000 | Ohno et al. |
| 6,165,515 A | 12/2000 | Matsuyama et al. |
| 6,365,192 B1 | 4/2002 | Konishi |
| 6,726,932 B2 | 4/2004 | Konishi |

FOREIGN PATENT DOCUMENTS

| EP | 0 300 973 A1 | 1/1989 |
| EP | 0 315 591 A2 | 5/1989 |
| EP | 0 341 209 A2 | 11/1989 |
| EP | 0 348 353 A2 | 12/1989 |
| EP | 0 621 038 A1 | 10/1994 |
| EP | 0 645 142 A1 | 3/1995 |
| EP | 0 733 636 A1 | 9/1996 |
| EP | 0 919 238 A2 | 6/1999 |
| EP | 0 953 352 A1 | 11/1999 |
| FR | 2 610 523 | 8/1988 |
| FR | 2 671 488 | 7/1992 |
| FR | 2 720 068 | 11/1995 |
| GB | 697351 | 9/1953 |
| JP | 53101515 | 9/1978 |
| JP | 55087724 | 7/1980 |
| JP | 57-077697 | 5/1982 |
| JP | 58 035117 | 1/1983 |
| JP | 1265028 | 10/1989 |
| JP | 1319422 | 12/1989 |
| JP | 2028119 | 1/1990 |
| JP | 3-43279 | 7/1991 |
| JP | 7097336 | 3/1995 |
| JP | 8291077 | 11/1996 |
| JP | 2594222 | 12/1996 |
| JP | 10194978 | 7/1998 |
| JP | 11139977 | 5/1999 |
| JP | 2000016942 | 1/2000 |
| JP | 11080005 | 12/2000 |
| JP | 2000336034 | 12/2000 |
| WO | WO 9813377 | 4/1998 |
| WO | WO 2004039383 | 5/2004 |

OTHER PUBLICATIONS

Shedlock et al., Nature Reviews Immunology, 2009, 9:717-728.*
Thomas, Nature Medicine, 2009, 15(8):855-859.*
Chaisson, The Body: The Complete HIV/AIDS Resource, Sep. 1996.*
McArthur et al., Journal of NeuroVirology, 2003, 9:205-221.*
MedPub Abstract of Daniel et al, "Simian Models for Aids," Cancer Detect Prev. Suppl., 1987; 1:501-7.
MedPub Abstract of Gardner, MB, "Animal Models of Aids," FASEB J., Dec. 1989; 3(14):2593-2606.
MedPub Abstract of "Animal Models for HIV Infection and AIDS: Memorandum From a WHO Meeting," Bull. World Health Organ., 1988; 66(5):561-57.
Jun. 28, 2007 Notification Concerning Transmittal of International Preliminary Report on Patentability.
Jun. 19, 2007 International Preliminary Report on Patentability (PCT/IB/373).
Apr. 26, 2006 Written Opinion of the International Searching Authority (PCT/ISA/237).
De Reuck J., et al., "A double-blind study of neurotropin in patients with acute ischemic stroke," *ACTA Neurologica Scandinavica* vol. 89, No. 5, 1994, pp. 329-335, XP002109696.
"Drugs in Japan, Ethical Drugs," Yakugyo Jiho Co., Ltd., 1994, p. 1434.
Fahey et al., "Status of Immune-based therapies in HIV infection and AIDS," *Clin. Exp. Immunol.* (1992) 88, 1-5.
Fujii, Y., et al., "Biological Overview of HIV Accessory Protein Nef," *Saibo Kogaku*, vo. 16, No. 1, pp. 94-99 (1997).

(Continued)

*Primary Examiner* — Zachariah Lucas
*Assistant Examiner* — Nicole Kinsey White
(74) *Attorney, Agent, or Firm* — Greenblum & Bernstein, P.L.C.

(57) ABSTRACT

A method for treatment of HIV infection includes administering at least one anti-HIV drug, such as a reverse transcriptase inhibitor, to a patient in need of such treatment and administering an extract from inflammatory tissue inoculated with vaccinia virus to the patient following the administration of the at least one anti-HIV drug. The extract maintains suppressive action on HIV replication, even if the administration of the anti-HIV drug is terminated.

12 Claims, 2 Drawing Sheets

OTHER PUBLICATIONS

Gabrielian, Japan J., *Cerebrovascular Injuries Induced by Activation of Platelets and Leukocytes in Vivo and Their Correction by Neurotropin*, Pharmacol., 60:51-54, 1992.

Kinter, A., et al., "Chemokines, cytokines, and HIV: . . ." Immunol. Rev. 177:88-98, 2000.

Lui et al., "Binding of HIV-1 Nef to a novel thioesterase enzyme correlates with Nef-mediated CD4 down-regulation," *The Journal of Biological Chemistry* vol. 272 (1997) pp. 13779-13785.

Luo T., et al., "Infectivity enhancement by immunodeficiency virus type 1 Nef is independent of its association with a celluar serine/threonine kinase," *Journal of Virology*, vol. 71, No. 12, 1997, pp. 9524-9530, XP002115666.

Mandell CP., "SIV/HIV Nef recombinant virus (SHIV nef) produces simian AIDS in rhesus macaques" *Virology*, 265(2):235-51 1999 Dec. 20, 1999, abst.

Okada H., et al. "Inhibition of HIV-1 Nef induced apoplosis of uninfected human blood cells by serine/threonine protein kinase inhibitors, etc.", *FEBS Letters*, vol. 422, No. 3, 1998, pp. 363-367, XP002115665.

Patent Abstracts of Japan, "Antiviral Agent", vol. 017, No. 225 (C-1055), May 10, 1993 & JP 04360838.

Piguet V., "The Nef protein of primate lentiviruses," *Rev Med Viro* 9(2):111-20 Apr.-Jun. 1999, abst.

Rossi F., et al., "HsN3 proteasomal subunit as a target for human immunodeficiency virus type 1 Nef protein," *Virology*, vol. 237, No. 1, 1997, pp. 33-45, XP002115667.

Section CH, Week 9645, Derwent, AN 96-450925 XP002109698 & JP 08 225452 A, Sep. 3, 1996, abst.

Shimizu et al., "Electrophysiological Study of Neurotropin-Induced Responses in Guinea Pig Hypothalamic Neurons", Br. Res. Bull., Dec. 1992, 29(6):767-72.

Smith, B.L. et al., "The HIV Nef protein associates with protein kinase C theta" *Journal of Biological Chemistry*, vol. 271, No. 28, pp. 16753-16757, XP002115668, (1996).

Sprumont, et al., "Morphometrical Quantification of Brain Edema Related to Experimental Multiple Micro-Infarcts in Mice: Assessment of Neurotropin Effect," *Meth Find Exp Clin Pharmacol* 1993, 15(3): 169-177, XP0021009697.

Takenoka, Y., et al., "Influence of Neurotropin on Thymic Microenviromental Abnormalities of NZB Mice," *Int. J. Immunotherapy*, XI(2), pp. 49-56 (1995).

Tanaka et al., *Int. Clin, Psychopharm*, 3(3): 239-44, Medline Abst. No. 91079456 (Jul. 1988).

"Updated DHHS Guidelines: Recommended Antiretroviral Agents for Treatment of Established HIV Infection" in Johns Hopkins AIDS Service: The Hopkins HIV Report, (May 1998) found online at: http://hopkins-aids.edu/publications/report/may98_2.html.

* cited by examiner

METHOD FOR TREATMENT OF HIV INFECTION

RELATED APPLICATIONS

This application is a 371 U.S. national stage application of international application PCT/US2005/045338 filed Dec. 15, 2005, which is a continuation-in-part of U.S. patent application Ser. No. 11/015,631 filed Dec. 17, 2004, now abandoned, the disclosure of which is herein incorporated by reference in its entirety.

BACKGROUND OF THE INVENTION

The present invention relates to a novel method for treatment of HIV infection by using an extract from inflammatory tissue inoculated with vaccinia virus. More particularly, it relates to a combined therapy for HIV infection with anti-HIV drugs and the extract.

Acquired Immunodeficiency Syndrome (AIDS) is a disease caused by infection of Human Immunodeficiency Virus (HIV), one species of lentivirus, which induces a progressive decrease in immune function leading ultimately to death. At present in the United States (as of August 2003), eight nucleoside/nucleotide reverse transcriptase inhibitors, three non-nucleoside reverse transcriptase inhibitors, seven protease inhibitors, and one fusion inhibitor are approved as anti-HIV chemotherapeutic drugs. A therapy using a combination of these drugs, named highly active antiretroviral therapy (HAART), is commonly used and standardized.

HAART can suppress the replication of HIV in an infected patient and can prevent the progress of HIV infection. However, it is necessary to suppress the replication of HIV completely for several decades to prevent the development of AIDS. The discontinuation of the chemotherapy at any time following injection causes a rebound in, and repopulation of, HIV. Thus, a patient is required to receive the chemotherapy continuously during most of his or her lifetime. It is difficult to take anti-HIV drugs continuously because anti-HIV drugs have a large formulation. As a result, many drugs must be taken at each dosage. Further, the anti-HIV drugs induce various and strong side effects. If a patient does not keep the dosage schedule very strictly, the treatment meets with failure by the induction of a drug-resistant virus.

As mentioned above, the continuous use of anti-HIV drugs for a long period of time in HIV infected patients, while keeping a consistent dosage schedule of almost 100%, has caused various problems, including the decrease of quality of life (QOL) for patients, economic burdens, and risk of long term toxicity. To avoid these problems, it is desirable to provide an alternative to continuous treatment of HIV-1 infected patients with conventional FDA approved anti-HIV chemotherapeutic drug regimens.

The pharmacological activities of an extract from an inflammatory tissue inoculated with vaccinia virus include: (1) analgesic, sedative, anti-stress and anti-allergic effects (Japanese Patent Laid-Open No. Sho-53-101515); (2) immuno-enhancing, anti-cancer and hepatocirrhosis suppressive effects (Japanese Patent Laid-Open No. Sho-55-87724); (3) therapeutic effect for idiopathic thrombocytopenic purpra (Japanese Patent Laid-Open No. Hei-1-265028); (4) therapeutic effects for post-herpetic neuralgia, brain edema, dementia, and spiro-cerebellar degeneration purpra (Japanese Patent Laid-Open No. Hei-1-319422, U.S. Pat. No. 5,013,558); (5) therapeutic effects for Raynaud syndrome, diabetic neuropathy, and sequelae of myelo-optico neuropathy (Japanese Patent Laid-Open No. Hei-2-28119); (6) inhibitory effect on kallikrein production and improving effect of peripheral circulatory disturbance (Japanese Patent Laid-Open No. Hei-7-97336, U.S. Pat. No. 5,560,935); (7) improving effect of bone atrophy (Japanese Patent-Laid-Open No. Hei-8-291077); (8) suppressive effect of nitrogen monoxide useful for therapy of sepsis and endotoxin shock (Japanese Patent Laid-Open No. Hei-10-194978, U.S. Pat. No. 6,051,613); (9) therapeutic effect for osteoporosis (Japanese Patent Laid-Open No. Hei-11-80005); (10) therapeutic effect for AIDS by Nef action inhibiting effect or chemokine-production increasing effect (Japanese Patent Laid-Open No. Hei-11-139977 or 2000-336034); (11) therapeutic effect for ischemic diseases such as cerebral infarction (Japanese Patent Laid-Open No. 2000-16942); and (12) therapeutic effect for fibromyalgia (International PCT Publication No. WO2004/039383).

An aspect of the present invention is to provide a method for treatment of HIV infection to offer an alternative to the problems associated with the long term use of anti-HIV drugs, such as the decrease of QOL of patients accompanied with therapy for HIV infection including AIDS, economical burdens, strong side effects of anti-retroviral drugs, and appearance of drug-resistant viruses. In particular, the present invention provides a novel adjunct method for the treatment of HIV to give persisting effectiveness to suppress HIV replication.

The present inventors have conducted various studies regarding the suppression on HIV replication for the therapy of HIV infection. As a result, the inventors found that after viral loads are lowered by the administrations of an approved anti-HIV drug, the suppressive action on HIV replication can be maintained by the administration of an extract from inflammatory tissue inoculated with vaccinia virus, during a time period during which the conventional anti-HIV drugs are terminated.

SUMMARY OF THE INVENTION

The present invention provides an alternative to continuous treatment of HIV-1 infected patients with conventional FDA approved anti-HIV chemotherapeutic drug regimens. Thus, patients can be administered the conventional anti-HIV chemotherapeutic drugs until the level of HIV in the blood is reduced to below detectable levels. Thereafter, the patients can be administered pharmaceutically effective dosages of an extract prepared from tissues that have been previously injected with vaccinia virus and demonstrate readily observable inflammatory responses. Such skin extracts can be administered without the requirement for the conventional anti-HIV chemotherapeutic drugs and have been shown to maintain the low to undetectable viral loads for a prolonged period of time thus providing the patients with a time period without conventional anti-HIV chemotherapy and in effect giving the patients a "drug holiday" thereby reducing the side effects and concurrently improving QOL with an opportunity to regenerate effective immunological effectiveness. In embodiments of the invention the extract may be administered during and after treatment with at least one anti-HIV drug. The administration of the extract may be initiated just prior to or after termination of treatment with the anti-HIV drug to maintain substantially reduced viral load or viral level of HIV-RNA for an extended period of time even after termination of treatment with the standard anti-HIV drug. In embodiments of the invention the administration of the extract may be initiated when the plasma viral level of HIV-RNA is lowered to less than a detectable limit by administration of the standard anti-HIV drug. The extract from the inflammatory tissue prepared from rabbit skin following vaccinia virus administration is combined with the standard anti-HIV drug such as a reverse transcriptase inhibitor to reduce treatment time with the standard anti-HIV drug.

DETAILED DESCRIPTION OF THE INVENTION

Figure 1:
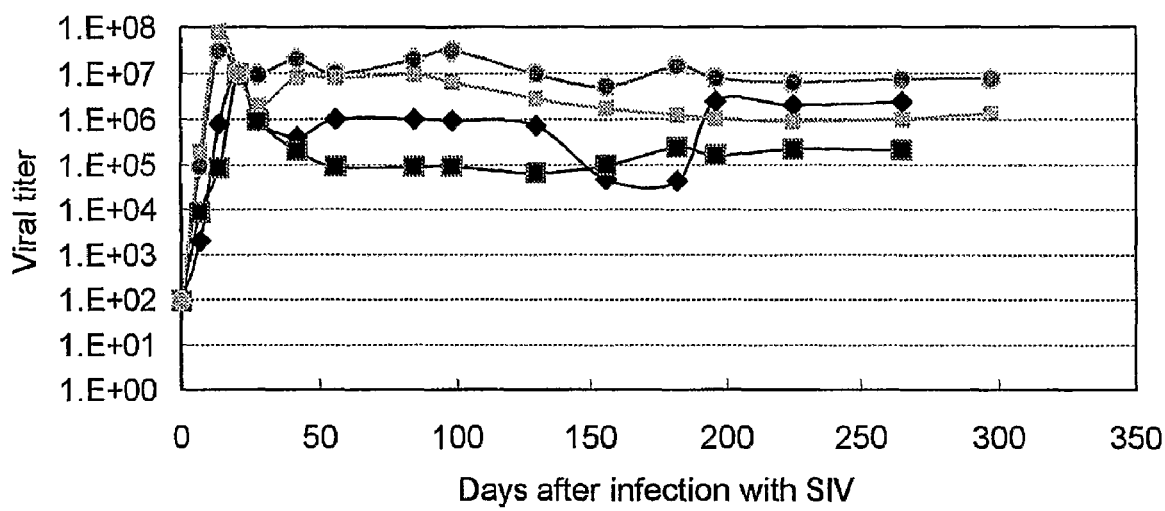
FIG. 1 shows a graph representing the levels of plasma viral loads in rhesus macaques without anti-HIV drug therapy after SIV infection.

According to the protocol outlined in the present invention, the suppressive action on HIV replication obtained by the administration of a previously approved anti-HIV drugs may be maintained by the administration of an extract prepared from inflammatory tissue of a rabbit inoculated with vaccinia virus. Approved anti-HIV drugs may cause various side effects and other problems and may not be administered continuously for a long term period of time. Nevertheless, in embodiments of the present invention, the suppressive action on HIV replication from the approved anti-HIV drugs may be maintained by administration of an extract from inflammatory tissue inoculated with vaccinia virus for a certain period following the reduction stage of virus level, even after the administrations of anti-HIV drugs are terminated. In embodiments of the present invention, the extract may be administered: (1) after viral loads of HIV in the blood of a patient are lowered by administration of at least one anti-HIV drug, or (2) after the plasma viral level of HIV-RNA is lowered to less than a detectable limit by administration of at least one anti-HIV drug.

The extract used according to the present invention is a safe drug having no problems such as the side effects observed in the anti-HIV drugs which are presently used. Therefore, the method of the present invention for treatment of HIV infection provides an effective alternative form of therapy to solve the problems noted above, such as the decrease of QOL of patients accompanied with the therapy for HIV infection including AIDS, economic burdens, strong side effects of anti-retroviral drugs, and the appearance of a drug-resistant virus.

An extract which may be used according to the present invention is an extract containing non-proteinaceous, bio-function-regulating substances produced in inflammatory tissue inoculated with vaccinia virus. There are various reports on the bio-active substances which are produced in an inflammatory tissue inoculated with vaccinia virus, methods for extracting such substances from diseased tissues, and the pharmacological activities thereof. The extracts, manufacturing methods of the extracts, and preferred doses thereof are disclosed in the patent publications discussed above. In addition, U.S. Pat. Nos. 5,013,558, 5,560,935, 6,051,613, and 6,165,515 are incorporated herein by reference in their entireties as to the extracts and active ingredients, manufacturing methods of the extracts, and doses disclosed therein. For example, as disclosed in U.S. Pat. No. 5,013,558 the extract may have the following physical and chemical properties: pale yellowish-brown, hygroscopic powder; soluble in water, methanol and ethanol; ultraviolet adsorption, $\lambda max=255$-275 nm; positive ninhydrin reaction; gives a blue color with amidol and ammonium molybdate; gives a green color with orcin and iron (II) ammonium sulfate; gives a precipitate with silver nitrate; and contains nucleic acid bases.

In embodiments of the present invention, animals for preparing the inflammatory tissues by inoculation of vaccinia virus include but are not limited to rabbits, cows, horses, sheep, goats, monkeys, rats, mice, guinea pigs, hamsters, swine, chickens, and the like.

The animal tissues used in the present invention may be cultured tissues, cultured cells or inflammatory tissues of human or animal origin which are infected with vaccinia virus, or chorio-allantoic membranes of embryonated eggs infected with virus. Examples of such cultured cells which may be utilized are various tissues (e.g., human hemocytes and placentae) and the cultured cells of various tissues such as kidney, skin, testis, lung, muscle, adrenal gland, thyroid gland, brain, nerve cells and hemocytes of the above-mentioned animals and embryos thereof. In preferred embodiments, the inflammatory tissues are inflammatory rabbit skin.

A commercially available drug preparation of an extract from inflammatory rabbit skin inoculated with vaccinia virus which may be employed in the present invention is described at pages 2499-2501 of "Drugs in Japan, Ethical Drugs" (27th ed., (2004)), edited by Japan Pharmaceutical Information Center, published by Yakugyo Jiho Co., Ltd. As described therein, this preparation is a drug containing non-proteinaceous active substances extracted and isolated from inflammatory skin of rabbits inoculated with vaccinia virus. This drug has been used for low back pain, neck-shoulder-arm syndromes, periarthritis scapulohumeralis, osteoarthritis, symptomatic neuralgia, itching accompanied with skin disorders (such as eczema, dermatitis and urticaria), allergic rhinitis, sequelae of subacute myelo-optico-neuropathy (such as coldness, pain and paresthesia/dysesthesia), post-herpetic neuralgia, and the like. The drug is approved as an ethical drug in the forms of injections (subcutaneous, intramuscular and intravenous) and in the form of tablets that are commercially available. This drug preparation is available in Japan and has the tradename NEUROTROPIN.

An extract from inflammatory tissue inoculated with vaccinia virus for use in the present invention may be produced by inoculating an animal with vaccinia virus to cause inflammation. The inflammatory tissues are finely cut; an extracting medium is added thereto; and tissue residues are removed. A procedure to remove proteins is carried out in which active ingredients are adsorbed to the adsorbent, and the adsorbed ingredients are eluted from the adsorbent. For example, an extract from inflammatory tissue inoculated with vaccinia virus may be produced by the following steps:

(a) An animal is inoculated with vaccinia virus and inflammatory tissues such as the skin is removed and finely cut. An extracting medium such as water, phenol water, saline, or phenol-added glycerin water is added thereto and then filtration or centrifugation is conducted to give an extracted solution (filtrate or supernatant).

(b) The extracted solution is adjusted to acidic pH and heated to remove proteins. The protein-removed solution is adjusted to alkaline pH and heated again, and then filtered or centrifuged.

(c) The resulting filtrate or supernatant is adjusted to acidic pH and adsorbed to an adsorbent such as active carbon or kaolin.

(d) An extracting solvent such as water or the like is added to the adsorbent and adjusted to alkaline pH to elute adsorbed ingredients to give an extract from inflammatory tissue inoculated with vaccinia virus. Then, if desired, the extraction may suitably be evaporated to dryness under reduced pressure or freeze-dried to make dried materials.

In embodiments, the inflammatory tissues may be removed, finely cut, and made into an emulsified suspension by adding 1 to 5 times as much extracting solvent thereto. Examples of the extracting solvent applicable include distilled water, physiologically saline solution, weakly acidic to weakly basic buffers, and the like. If necessary, stabilizers such as glycerol; antibacterial/antiseptic agents such as phenol; and inorganic salts such as sodium chloride, potassium chloride, or magnesium chloride may be added thereto. At that time, the extraction can be facilitated with a treatment by freezing/melting, ultrasonic waves, cell membrane dissolving enzymes or surface-active agents to cause cell destructions.

The resulting milky extract may be filtered or centrifuged to remove tissue residues and then proteins may be removed therefrom. Removal of proteins can be carried out by known methods, for example, heating; treatments with protein denaturing agents such as acids, bases, urea, guanidine, organic solvents such as acetone, surface-active agents, and the like; isoelectric precipitation; salting-out; and the like. Then, the precipitated proteins may be removed, for example, by filtration using filter paper (cellulose, nitrocellulose, and the like), glass filter, Celite or a Seitz filter, ultrafiltration, centrifugation, and the like.

The obtained extract containing ingredients may be adjusted to an acidic pH, preferably to a pH of 3.5 to 5.5, by acids such as hydrochloric acid, sulfuric acid, and hydrobromic acid, and may be adsorbed with an adsorbent. As an adsorbent, activated charcoal, kaolin, and the like may be employed. The adsorbents may be added to the extract followed by stirring or the extract may be passed through a column filled with the adsorbents, whereby active ingredients can be adsorbed.

To elute the ingredients from the adsorbents, an eluting solvent may be added to the adsorbents and eluted at room temperature or with heating to some extent or with stirring. The adsorbents may be removed by conventional means such as filtration and centrifugation to complete the elution. As an eluting solvent, water, methanol, ethanol, isopropanol or a mixture thereof which may be adjusted to basic pH may be employed. Preferably, water adjusted to a pH of 9 to 12 can be used.

The extract (eluted solution) produced as above can be prepared to desired formulations for raw materials or medicines. For example, the solution may be adjusted to neutral pH to prepare raw materials of drugs, and may be adjusted to desired concentrations by condensation or dilution. Furthermore, in order to prepare an injection, the solution may be prepared to an isotonic solution the same as saline. The solution may be prepared to solid preparations available for raw materials of tablets and the like by concentration to dryness or lyophilization.

As a method of administration, oral and other administrations such as subcutaneous, intramuscular and intravenous administrations may be used. The dosage to be utilized is dependent on the kind of extraction procedure utilized from the inflammatory tissue inoculated with vaccinia virus. The dose which is approved in the commercially available preparation according to "Drugs in Japan, Ethical Drugs" (page 2499) is, principally, 16 NU per day and 3.6-7.2 NU per day by oral administration and by injection, respectively. However, the dose or pharmaceutically effective amount may be appropriately increased or decreased depending upon the type of the disease, degree of seriousness, individual difference in the patients, method of administration, period of administration, and the like (NU: Neurotropin unit). Neurotropin unit is defined by $ED_{50}$ value of analgesic effect measured by a modified Randall-Selitto method using SART-stressed mice. The SART-stressed mice are chronic stressed animals showing a lowered pain threshold than a normal animal. One NU indicates the activity of 1 mg of analgesic ingredients in Neurotropin preparations when the $ED_{50}$ value is 100 mg/kg of the preparation.

As an anti-HIV drug used in the method for treatment of the present invention, any drugs having a reducing action on viral loads of HIV in blood can be used. In embodiments, nucleoside/nucleotide analogue reverse transcriptase inhibitors such as Abacavir (ABC), Didanosine (ddI), Emtricitabine (FTC), Lamivudine (3TC), Stavudine (d4T), Tenofovir (TDF), Zalcitabine (ddC) and Zidovudine (AZT); non-nucleoside reverse transcriptase inhibitors such as Delavirdine (DLV), Efavirenz (RFV) and Nevirapine (NVP); protease inhibitors such as Amprenavir (APV), Atazanavir (ATV), Indinavir (IDV), Ritonavir (RTV), Lopinavir/Ritonavir (LPV/RTV), Nelfinavir (NFV) and Saquinavir (SQV); and fusion inhibitors such as Enfuvirtide (T20) can be employed as conventional anti-retroviral drugs which are already approved for use in HIV infection in the United States. In preferred embodiments, a combination of the anti-HIV drugs may be used, however, the method of the present invention is not limited thereto. The dose or pharmaceutically effective amount, administration route, the number of administrations, and the like of the HIV-drugs can be determined according to various conditions.

The anti-HIV drugs and the extract from inflammatory tissue inoculated with vaccinia virus may each be used in pharmaceutically effective amounts for treating humans or animals, such as mammals, in need of treatment for HIV infection.

The following non-limiting examples illustrate manufacturing methods for producing an extract from inflammatory tissue inoculated with vaccinia virus, and pharmacological studies. All parts, percentages and ratios are by weight, all temperatures are in ° C., and all reactions are conducted at about atmospheric pressure and room temperature unless indicated to the contrary. In the following Examples 2 and 3, the dryness in vacuo is conducted in the final steps. However, this procedure is for making tablets and, therefore, is not indispensable. The results of pharmacological studies show a persisting effect for suppressing the proliferation of retrovirus for treatment of HIV infection:

EXAMPLE 1

Skins of healthy adult rabbits were inoculated with vaccinia virus to cause inflammation. The inflammatory skins were removed, finely cut and phenol water was added thereto. The mixture was filtered with pressure, and the resulting filtrate was adjusted to pH 5 with hydrochloric acid and then heated at 90-100° C. for 30 minutes. Proteins were removed by filtration, the filtrate was adjusted to pH 9 with sodium hydroxide, further heated at 90-100° C. for 15 minutes and filtered. The filtrate was adjusted to about pH 4, stirred for 2 hours after adding 2% of activated charcoal, and centrifuged. The resulting activated charcoal was mixed with water, adjusted to pH 10 with sodium hydroxide, stirred at 60° C. for 1.5 hours and centrifuged to give a supernatant. The activated charcoals precipitated by centrifugation were mixed with water, adjusted to pH 11 with sodium hydroxide, stirred at 60° C. for 1.5 hours and centrifuged to give a supernatant. Both of the supernatants obtained were combined and neutralized with hydrochloric acid to give an extract from inflammatory tissue inoculated with vaccinia virus. In the following pharmacological studies, the extract was adjusted to appropriate concentrations to be used.

EXAMPLE 2

Skins of healthy adult rabbits were inoculated with vaccinia virus to cause inflammation. The inflammatory skins were aseptically removed, finely cut and phenol-added glycerin water was added thereto. The mixture was ground using a homogenizer to prepare an emulsion. The emulsion was filtered with centrifugation, and the resulting filtrate was adjusted to pH 4.8-5.5 with hydrochloric acid, heated at 100° C. with a steam flow and then filtered. The filtrate was further filtered with Seitz filter, adjusted to pH 9.2 with sodium hydroxide, heated at 100° C. and filtered. The filtrate was adjusted to pH 4.5, stirred for 1-5 hours after adding 1.5% of activated charcoal, and filtered. The activated charcoal was mixed with water, adjusted to pH 9.4-10 with sodium hydroxide, stirred for 3-5 hours and filtered. The resulting filtrate was neutralized with hydrochloric acid and dried in vacuo.

EXAMPLE 3

Skins of healthy adult rabbits were inoculated with vaccinia virus to activate or stress the tissues. The activated skins were aseptically removed, finely cut and water was added thereto. The mixture was ground using a homogenizer to prepare an emulsion. The emulsion was filtered with pressure, and the resulting filtrate was adjusted to pH 5.0 with hydrochloric acid and heated at 100° C. with a steam flow. Proteins were removed by filtration, the filtrate was adjusted to pH 9.1 with sodium hydroxide, heated at 100° C. and filtered. The filtrate was adjusted to pH 4.1, stirred after adding 2% of activated charcoal, and the mixture was filtered to obtain a filtrate and a first batch of recovered activated charcoal. To the filtrate was added 5.5% of activated charcoal and the mixture was stirred for 2 hours, and filtered to obtain a second batch of recovered activated charcoal. The first batch of recovered activated charcoal was mixed with water, adjusted to pH 9.9 with sodium hydroxide, stirred at 60° C. for 1.5 hours and filtered. Water was then added to the first batch of the activated charcoal and to the second batch of activated charcoal. The pH of each batch was then adjusted to pH 10.9 with sodium hydroxide, and each batch was stirred at 60° C. for 1.5 hours and then filtered. The resulting filtrates were combined, neutralized with hydrochloric acid, desalted using electrodialysis with membrane (molecular weight: 100), and dried in vacuo.

EXAMPLE 4

Pharmacological Study

A correlative pharmacological study regarding a method for treatment of HIV infection according to the present invention, namely an anti-retroviral action, was conducted. The pharmacological study was performed to determine the effectiveness of an extract from inflammatory tissue inoculated with vaccinia virus to influence the levels of viral rebound in SIV (Simian Immunodeficiency Virus)-infected monkeys following a standard 28 day single cycle anti-retroviral drug therapy.

This pharmacological study included a total of 3 groups of rhesus macaques (*Macaca mulatta*) of Indian origin with 4 monkeys included in each group. Group 1 included the monkeys (Virus control) that were not treated by an anti-retroviral drug after SIV infection. The monkeys in Group 2 (PMPA control) received a single 28 day cycle of daily administration of an anti-retroviral drug. The monkeys in Group 3 (Extract treatment) were administered an extract prepared from inflammatory tissue inoculated with vaccinia virus following a single 28 day cycle of daily administration of the same anti-retroviral drug as Group 2 monkeys. For each group, the studies were performed as follows:

(1) Virus Infection (All Groups)

A single large batch of SIVmac239 was grown in day 3 rhesus PHA blasts. The supernatant fluids were ultracentrifuged, and the resulting virus was purified on a sucrose gradient and then pelleted. The pelleted virus was then resuspended in 1.0 mL of PBS (phosphate buffered saline) and termed virus stock. The level of virus was determined and the level of replication competent virus was titrated.

The stock virus was then diluted so as to contain approximately 200 $AID_{50}$ (50% animal infectious dose) in a volume of 1.0 mL, and each animal in each group was injected intravenously with 1.0 mL of the virus solution to infect with SIV.

(2) Determination of Viral Load Set Point (All Groups)

Following SIV infection, each animal was bled approximately 1.0 mL on days 0, 7, 14, 21, 28, 42 and 56 post infection and the viral level was quantified by real time PCR. The viral copy number per ml was recorded and viral load set point was determined as a value that reaches a plateau following increased viral level following initial viral load spike.

(3) PMPA Therapy (Groups 2 and 3)

PMPA (9-R-(2-phophorylmethoxypropyl) adenine) is the standard drug for anti-retroviral chemotherapy of SIV infected non-human primates. The monkeys of Group 2 (PMPA control) and Group 3 (Extract treatment) were subcutaneously administered with PMPA at a dose of 30 mg/kg daily for 28 days soon after they reached viral load set point and the levels of plasma viral loads was determined. PMPA administration at a dose of 30 mg/kg daily for 28 days was decided because it was previously determined to be an effective dose regimen that leads to a reduction of plasma and cellular viral loads to almost undetectable levels.

(4) Administration of an Extract from Inflammatory Tissue Inoculated with Vaccinia Virus (Group 3)

An extract from inflammatory tissue inoculated with vaccinia virus produced in Example 1 was administered to the monkeys of Group 3 (Extract treatment) to determine the effectiveness of the extract to influence the level of plasma viremia following the anti-retroviral drug therapy. The extract from inflammatory tissue inoculated with vaccinia virus was adjusted to the appropriate concentration and sonicated for 20 minutes at 60° C. and filtered through a 0.45-μm filter. It was then administered subcutaneously at a dose of 3.3 NU/kg daily for 60 days initiated at 2 days prior to the termination of PMPA therapy and the level of plasma viral loads were continuously monitored.

(5) Evaluation of Each Animal Response Prior to the Infection Study

A blood sample of each rhesus macaque was collected prior to the above pharmacological study, and each peripheral blood mononuclear cell (PBMC) was isolated and cultivated for defining the optimal concentration of PHA (phytohemagglutinin) that induced the maximum proliferation of PBMC. The proliferation study of PBMC was performed using 20% of the optimal concentration of PHA in the presence of various concentrations of the extract from inflammatory tissue inoculated with vaccinia virus. Then, each concentration of the chemokine such as RANTES, MIP-1α or MIP-1β in the supernatant fluid of the culture was determined. For example, in 2 monkeys among 4 it was confirmed that the production of RANTES in the presence of 10-50 mNU of the extract from inflammatory tissue inoculated with vaccinia virus was higher than the production of RANTES with the use of the optimal concentration of PHA (in the absence of the extract). Also, the production of MIP-1β was increased in the presence of the extract from inflammatory tissue inoculated with vaccinia virus, but the increased rate was not higher than that of RANTES.

(6) Results

Figure 2:
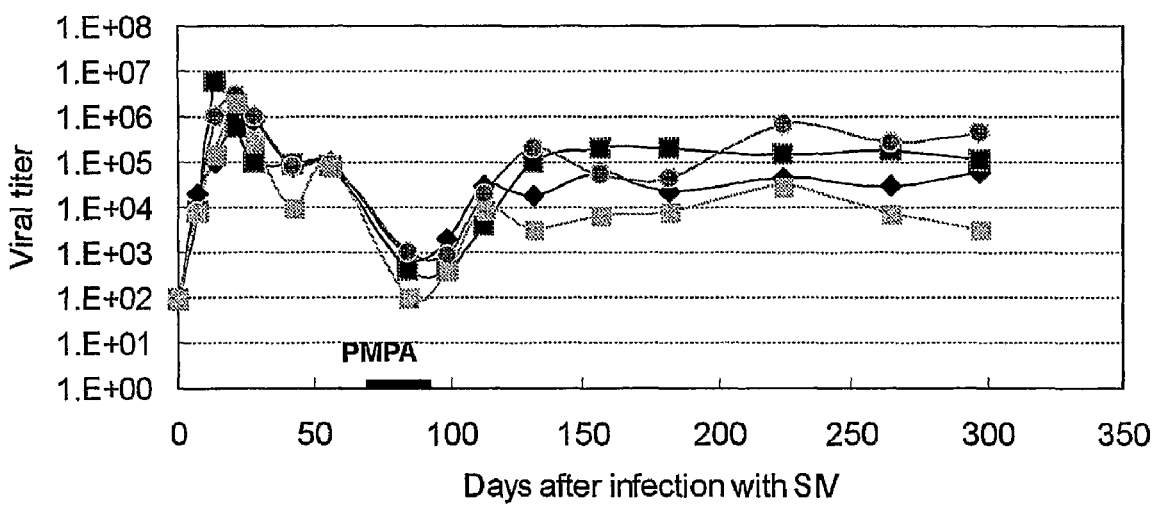
FIG. 2 shows a graph representing the levels of plasma viral loads in rhesus macaques with only the standard anti-HIV drug PMPA (9-R-(2-phophorylmethoxypropyl) adenine) therapy administered following SIV infection.
Figure 3:
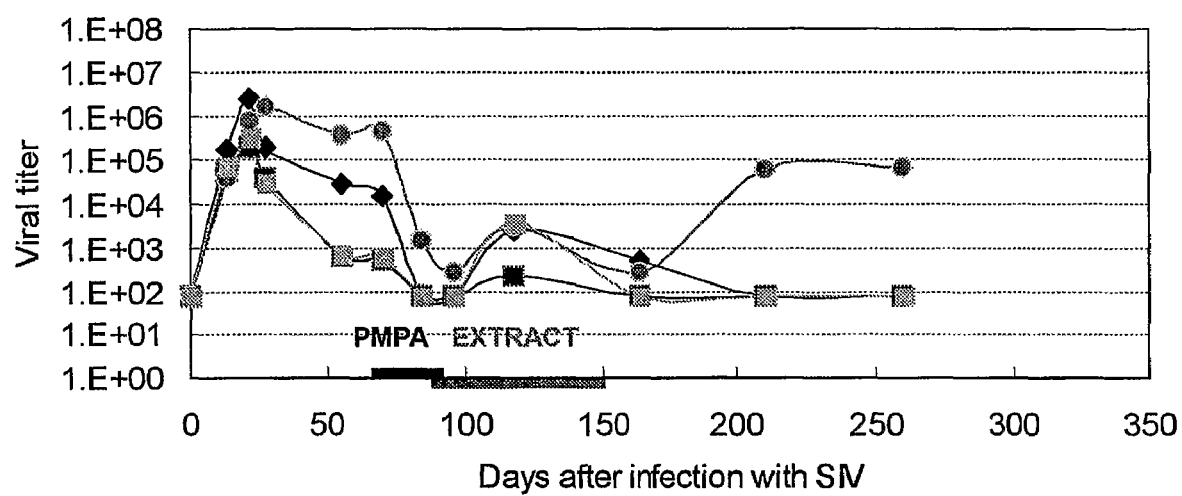
FIG. 3 shows a graph representing the levels of plasma viral loads in rhesus macaques in which the administration of an extract from inflammatory tissue inoculated with vaccinia virus was initiated just before the termination of PMPA therapy after SIV infection.

The graphs representing the levels of plasma viral loads after the infection of SIV of each group according to the above-mentioned procedures are shown for each monkey in FIGS. 1-3.

The plasma viral loads after infection with SIV ranged from 100,000 to 10 million viral copies per mL at peak and then reached a set point 6-8 weeks post infection. The viral loads in Group 1 (Virus control) without any therapy at this point stayed at the set point (FIG. 1). However, PMPA therapy led to a marked reduction in plasma viral loads to between 100 to 1000 viral copies per mL by day 28 in Group 2 (PMPA control) and in Group 3 (Extract treatment).

Thereafter, in Group 2 (PMPA control) in which no further treatment was continued following the termination of PMPA therapy, it appeared that viral loads rebounded soon after the discontinuation of PMPA therapy (FIG. 2). On the other hand, in Group 3 (Extract treatment) in which the administration of an extract from inflammatory tissue inoculated with vaccinia virus was initiated just before the termination of PMPA therapy, it was possible to keep the suppression of viral loads for a long period of time even if the administration was stopped after only 60 days (FIG. 3).

In addition, the result of chemokines production such as RANTES or MIP-1β in the preserved plasma of the above monkeys was compared with the result of the above-mentioned infection study. Consequently, the increase of chemokines was observed along with the suppression of virus load in the plasma in the animal group showing significant viral suppression. As a distinct correlation regarding RANTES was confirmed in particular, the increase of RANTES was thought to be related to the suppression of virus. The production of chemokines differed in individual animals in the study to evaluate the response to chemokines production prior to the infection study. This suggested that it was possible to make a prior evaluation of the effectiveness of the present method for treatment by determining the ability to enhance the production of chemokines such as RANTES in the cultivation study wherein PBMC was obtained from the patient before the treatment and cultivated in the presence of the extract from inflammatory tissue inoculated with vaccinia virus. In this manner, the effectiveness of treatment with the extract may be evaluated before treatment of a patient in need of treatment for HIV infection, and patients in need of treatment for HIV infection may be screened for effective treatment with the extract.

As apparent from the results of the above pharmacological studies, it is demonstrated that, according to the method of the present invention for treatments of HIV infection, the suppressive action on HIV replication can be maintained by the administration of an extract from inflammatory tissue inoculated with vaccinia virus for a certain period following the achievement of reduced viral loads induced by the administrations of anti-HIV drugs (i.e., the anti-HIV drugs were only administered daily for 28 days). The longer the approved anti-HIV drugs are used, the more problems have been noted to occur, such as strong side effects, appearance of resistant virus to the drug, decrease of QOL of patients, and economical burdens.

Therefore, since the suppressive effect on HIV proliferation caused by anti-HIV drugs can be maintained by use of an extract from inflammatory tissue inoculated with vaccinia virus for a short term, which has no problems such as side effects observed in the usual anti-HIV drugs, the method of the present invention for treatment of HIV infection is a useful adjunct therapy to solve the problems as mentioned above.

What is claimed is:

1. A method for treatment of HIV infection comprising:
    administering at least one anti-HIV drug to a patient in need of such treatment; and
    administering an extract from inflammatory tissue inoculated with vaccinia virus to the patient following the administration of the at least one anti-HIV drug, wherein the inflammatory tissue comprises skin tissue of a rabbit, and wherein the extract has the following physical and chemical properties:
    pale yellowish-brown, hygroscopic powder;
    soluble in water, methanol and ethanol;
    ultraviolet adsorption, λmax=255-275 nm;
    positive ninhydrin reaction;
    gives a blue color with amidol and ammonium molybdate;
    gives a green color with orcin and iron (II) ammonium sulfate;
    gives a precipitate with silver nitrate; and
    contains nucleic acid bases; and
    the administration of at least one anti-HIV drug is terminated and the extract maintains suppressive action on HIV replication.

2. A method according to claim 1 wherein the at least one anti-HIV drug is at least one drug selected from the group consisting of nucleoside/nucleotide reverse transcriptase inhibitors, non-nucleoside reverse transcriptase inhibitors, protease inhibitors, and fusion inhibitors.

3. A method according to claim 1 wherein the at least one anti-HIV drug comprises a reverse transcriptase inhibitor.

4. A method according to claim 3 wherein the reverse transcriptase inhibitor is at least one member selected from the group consisting of Abacavir (ABC), Didanosine (ddI), Emtricitabine (FTC), Lamivudine (3TC), Stavudine (d4T), Tenofovir (TDF), Zalcitabine (ddC), Zidovudine (AZT), Delavirdine (DLV), Efavirenz (RFV), and Nevirapine (NVP).

5. A method according to claim 1 wherein viral loads of HIV in the blood of the patient are lowered by administration of the at least one anti-HIV drug.

6. A method according to claim 1 wherein the plasma viral level of HIV-RNA is lowered to less than a detectable level by the administration of at least one anti-HIV drug.

7. A method for treatment of HIV infection comprising reducing the viral load of HIV in the blood or reducing the plasma viral level of HIV-RNA in a patient by the administration of a pharmaceutically effective amount of at least one anti-HIV drug, and administering a pharmaceutically effective amount of an extract from inflammatory tissue inoculated with vaccinia virus while said viral load of HIV or viral level of HIV-RNA is reduced, wherein the inflammatory tissue comprises skin tissue of a rabbit, and wherein the extract has the following physical and chemical properties:
    pale yellowish-brown, hygroscopic powder;
    soluble in water, methanol and ethanol;
    ultraviolet adsorption, λmax=255-275 nm;
    positive ninhydrin reaction;
    gives a blue color with amidol and ammonium molybdate;

gives a green color with orcin and iron (II) ammonium sulfate;
gives a precipitate with silver nitrate; and
contains nucleic acid bases, and
wherein said administration of said extract is initiated just prior to termination of treatment or after termination of treatment with said at least one anti-HIV drug.

8. A method according to claim 7 wherein said extract is administered during and after treatment with said at least one anti-HIV drug.

9. A method according to claim 7, wherein said administration of said extract is initiated when the plasma viral level of HIV-RNA is lowered to less than a detectable limit by administration of the at least one anti-HIV drug, the inflammatory tissue is skin tissue of rabbit, and the anti-HIV drug comprises a reverse transcriptase inhibitor.

10. A method for treatment of HIV infection comprising obtaining peripheral blood mononuclear cells from a patient in need of treatment of HIV infection prior to the treatment, cultivating the cells in the presence of an extract from inflammatory tissue inoculated with vaccinia virus, wherein the inflammatory tissue comprises skin tissue of a rabbit, and wherein the extract has the following physical and chemical properties:

pale yellowish-brown, hygroscopic powder;
soluble in water, methanol and ethanol;
ultraviolet adsorption, $\mu max=255\text{-}275$ nm;
positive ninhydrin reaction;
gives a blue color with amidol and ammonium molybdate;
gives a green color with orcin and iron (II) ammonium sulfate;
gives a precipitate with silver nitrate; and
contains nucleic acid bases,
cultivating the cells in the absence of said extract, and if said cultivation shows an increase in the production of a chemokine in the presence of said extract compared to the production of said chemokine in the absence of the extract, administering said extract to the patient following the administration of at least one anti-HIV drug.

11. A method according to claim 10, wherein said cultivation shows an increase in the production of RANTES compared to the production of RANTES in the absence of the extract.

12. A method according to claim 10, wherein said cultivation shows an increase in the production of MIP-1β compared to the production of MIP-1β in the absence of the extract.

* * * * *